(12) United States Patent
Quinn et al.

(10) Patent No.: US 7,813,889 B2
(45) Date of Patent: Oct. 12, 2010

(54) GUIDING IR TEMPERATURE MEASURING DEVICE WITH PROBE COVER

(75) Inventors: David E. Quinn, Auburn, NY (US); John A. Lane, Weedsport, NY (US); Scott A. Martin, Warners, NY (US); Craig M. Meyerson, Syracuse, NY (US); Matthew D. Mullin, Memphis, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 382 days.

(21) Appl. No.: 12/014,848

(22) Filed: Jan. 16, 2008

(65) Prior Publication Data

US 2009/0182526 A1 Jul. 16, 2009

(51) Int. Cl.
*G01J 5/10* (2006.01)
(52) U.S. Cl. ...................................... 702/131
(58) Field of Classification Search .................. 702/48, 702/49, 66, 67, 72, 85, 94, 99, 103, 106, 702/116, 119, 130, 131, 135, 136, 183, 189; 600/301, 310, 315, 373, 474, 549; 374/120, 374/121
See application file for complete search history.

(56) References Cited

U.S. PATENT DOCUMENTS

| | | | |
|---|---|---|---|
| 4,009,707 A | 3/1977 | Ward | |
| 6,022,140 A | 2/2000 | Fraden et al. | |
| 6,631,287 B2 | 10/2003 | Newman et al. | |
| 6,898,457 B1* | 5/2005 | Kraus et al. | 600/474 |
| 7,354,399 B2 | 4/2008 | Strom et al. | |
| 2002/0143257 A1* | 10/2002 | Newman et al. | 600/474 |
| 2003/0099277 A1* | 5/2003 | Bellifemine | 374/121 |
| 2003/0171655 A1 | 9/2003 | Newman et al. | |
| 2004/0124359 A1 | 7/2004 | Hamrelius et al. | |
| 2005/0117624 A1* | 6/2005 | Hollander et al. | 374/120 |

* cited by examiner

*Primary Examiner*—Mohamed Charioui
(74) *Attorney, Agent, or Firm*—Sonny Z. Zhan

(57) ABSTRACT

The invention relates to an Infrared (IR) thermometer including an IR detector configured to provide an IR emission data representative of a temperature of an area of tissue. The IR thermometer also includes one or more secondary sensors configured to provide an IR thermometer positioning data. At least one microcomputer is configured to receive the IR thermometer positioning data from one or more secondary sensors. The at least one microcomputer is configured to run an algorithm to convert the IR thermometer positioning data to an IR thermometer positioning indication, wherein the IR thermometer positioning indication suggests a direction to move the IR thermometer for a substantially optimal IR detector view of the area of tissue. The invention also relates to a guiding means including a positioning sensor and a display of IR thermometer positioning information, and a method for positioning an IR thermometer.

24 Claims, 13 Drawing Sheets

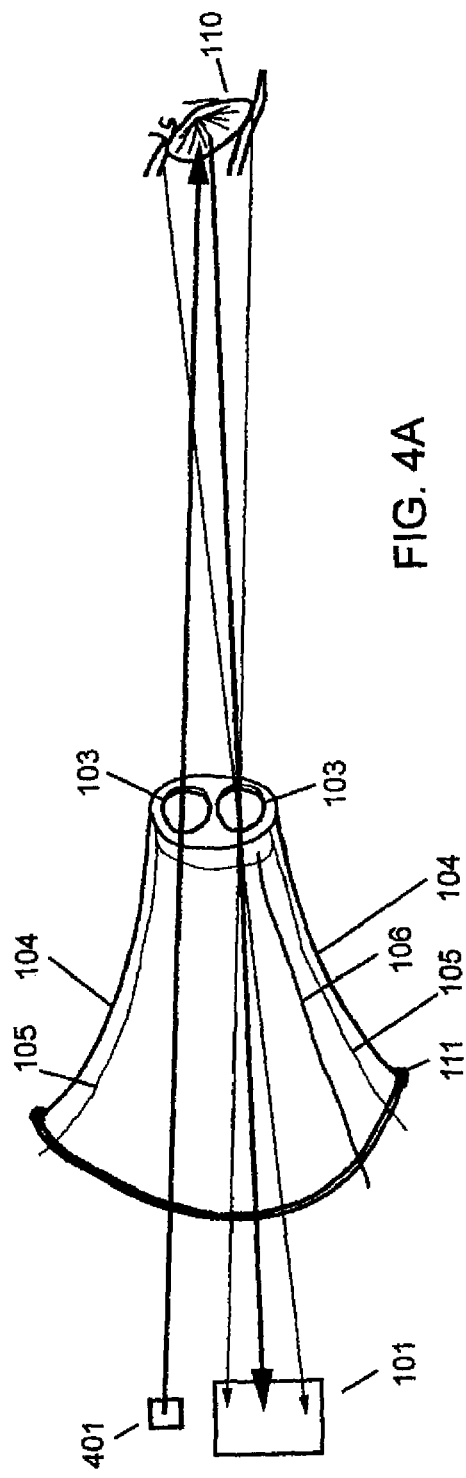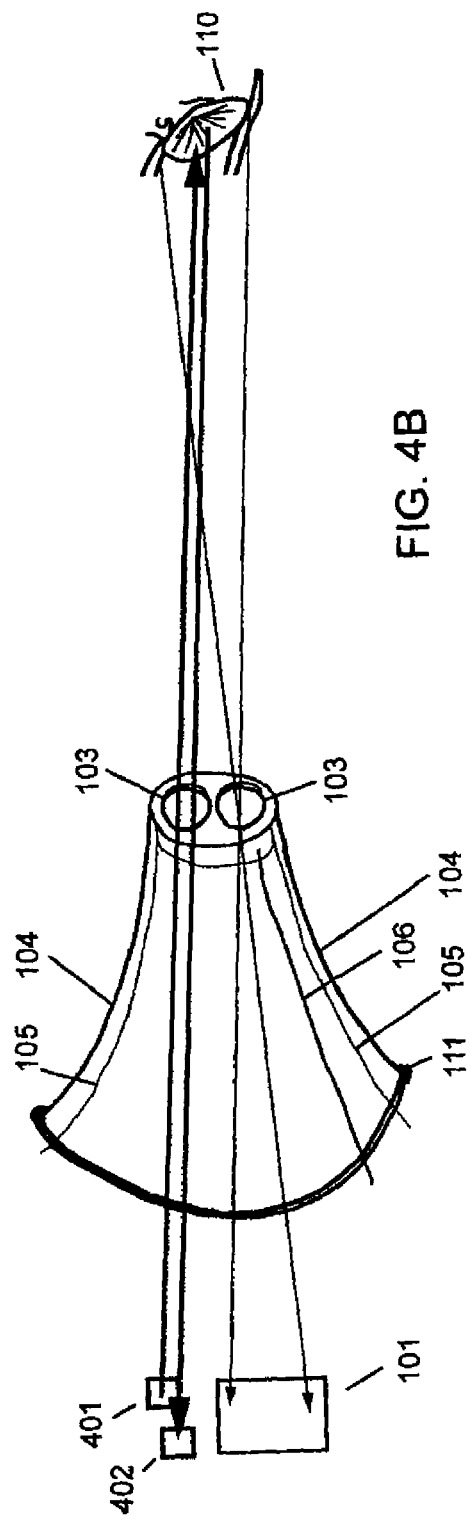

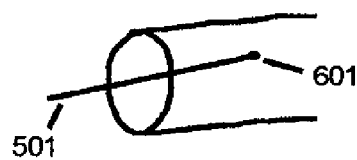 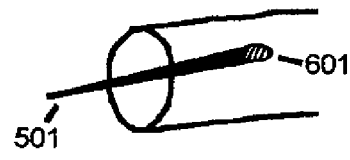
FIG. 6A  FIG. 6B
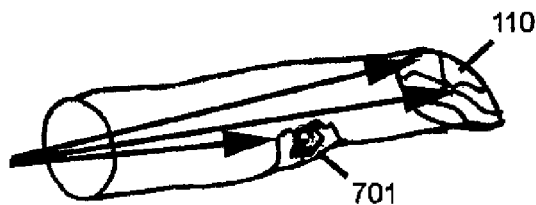
FIG. 7A
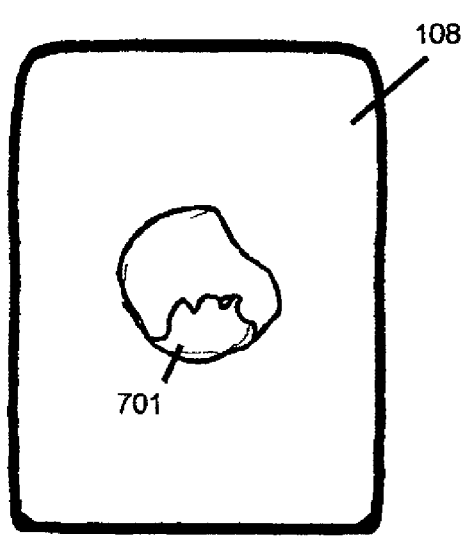 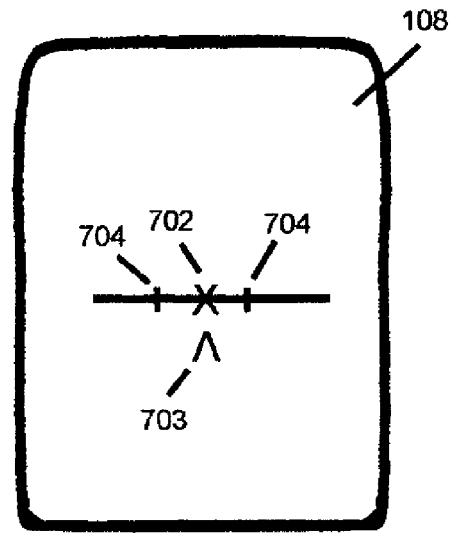
FIG. 7B  FIG. 7C

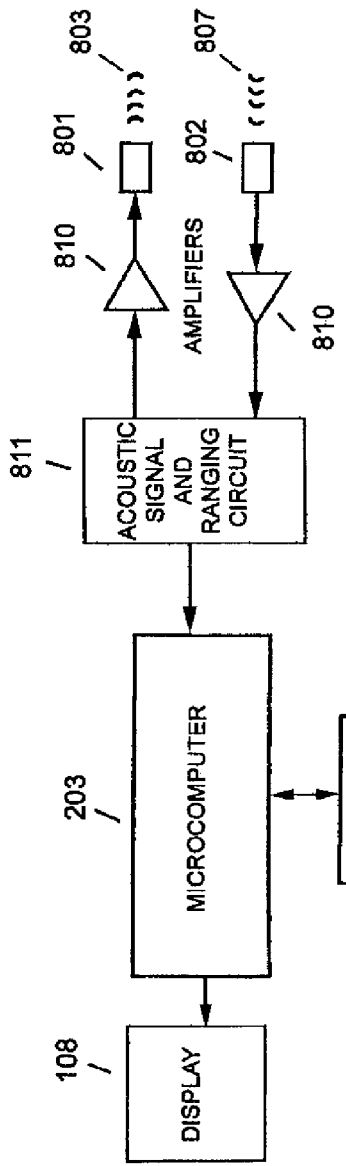
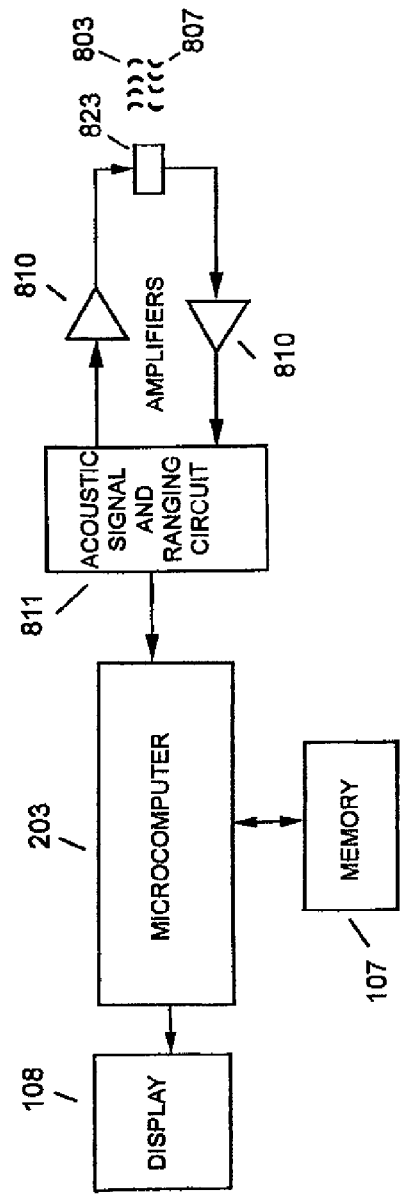

GUIDING IR TEMPERATURE MEASURING DEVICE WITH PROBE COVER

FIELD OF THE INVENTION

This invention relates generally to an IR thermometer and more particularly to a medical IR thermometer including guiding assistance.

BACKGROUND OF THE INVENTION

Infrared (IR) thermometers have been used to measure body temperature. Human IR temperature measurements are typically made by placing an IR detector in the vicinity of a person's ear canal, also known as the auditory canal. Generally such IR thermometers include a tapered conical probe section situated over or adjacent to an IR detector for ease of placement of the tip of the thermometer probe into the opening of a person's auditory canal.

The most accurate representation of the temperature of the human body has been found to be presented by the surface of the ear drum, the tympanic membrane. The temperature at various other locations on the surface of the auditory canal fall off moving away from the tympanic membrane. The temperature readings are typically the lowest at the walls of the auditory canal, particularly at the walls of the auditory canal outside of the skull wall and towards the auricle, the outer exposed surface of the ear.

The tapered conical section probe and the IR sensor can define a sensitive measurement axis substantially through the center of the tapered conical section. The problem is that to achieve a most accurate temperature measurement, the IR detector and the sensitive measurement axis should be properly aligned for an optimal view of the tympanic membrane while reading only a minimal IR contribution from the wall of the ear canal.

In one solution described in U.S. Pat. No. 6,631,287, commonly owned by the assignee of the present invention, the Welch Allyn Corporation of Skaneateles Falls, N.Y., the hottest temperature in a field of view of an IR sensor array was located in order to assist in positioning an IR probe. While there are merits to this approach, it might not always be the case that the hottest temperature in any given field of view gives the best placement of the IR probe in the auditory canal for a most optimal view of the tympanic membrane.

What is needed is an IR probe orientation system and method that can guide a user of an IR thermometer to achieve a physical positioning of an IR probe in an auditory canal for an optimized field of view of the tympanic membrane.

SUMMARY OF THE INVENTION

In one aspect the invention relates to an Infrared (IR) thermometer including an IR detector configured to provide an IR emission data representative of a temperature of an area of tissue. The IR thermometer also includes one or more secondary sensors configured to provide an IR thermometer positioning data. The IR thermometer also includes at least one microcomputer coupled to the IR detector, the at least one microcomputer configured to receive the IR emission data from the IR detector. The at least one microcomputer runs software including an algorithm to convert the IR emission data to a temperature measurement of the area of tissue. The at least one microcomputer is also coupled to the one or more secondary sensors, the at least one microcomputer also configured to receive the IR thermometer positioning data from the one or more secondary sensors. The at least one microcomputer is configured to run an algorithm to convert the IR thermometer positioning data to an IR thermometer positioning indication, wherein the IR thermometer positioning indication suggests a direction to move the IR thermometer for a substantially optimal IR detector view of the area of tissue.

In one embodiment, the one or more secondary sensors comprise one or more optical sensors.

In another embodiment, the one or more optical sensors comprise one or more two dimensional (2D) optical imagers.

In yet another embodiment, the one or more optical sensors comprise one or more one dimensional (1D) optical imagers.

In yet another embodiment, the algorithm to convert the IR thermometer positioning data to an IR thermometer positioning indication includes analyzing the IR thermometer positioning data from the one or more secondary sensors to determine one or more distances based on optical focus.

In yet another embodiment, the algorithm to convert the IR thermometer positioning data to an IR thermometer positioning indication includes analyzing the IR thermometer positioning data from the one or more secondary sensors to determine one or more distances based on optical ranging.

In yet another embodiment, the algorithm to convert the IR thermometer positioning data to an IR thermometer positioning indication includes a display of an image of substantially the same field of view of the IR detector.

In yet another embodiment, the image is an actual 1D or 2D image of the area of tissue in a field of view of the IR detector as viewed by an optical imager.

In yet another embodiment, the 1D or 2D image is a pre-stored 2D image selected by the algorithm as representative of the field of view most likely being viewed by the IR detector.

In yet another embodiment, further including a probe cover, the probe cover including at least one optical lens.

In yet another embodiment, the one or more secondary sensors comprise one or more acoustic sensors.

In yet another embodiment, the one or more acoustic sensors comprise one or more acoustic receivers and acoustic transmitters.

In yet another embodiment, the one or more acoustic sensors comprise one or more acoustic transceivers.

In yet another embodiment, the algorithm to convert the IR thermometer positioning data to an IR thermometer positioning indication includes analyzing the IR thermometer positioning data from the one or more secondary sensors to determine one or more distances based on acoustic ranging.

In yet another embodiment, the acoustic ranging includes a measurement of time differences between transmitted and received acoustic signals.

In yet another embodiment, the acoustic ranging includes a range measurement based on phase differences between transmitted and received acoustic signals.

In yet another embodiment, the acoustic ranging includes a range measurement based on wave-shape differences between transmitted and received acoustic signals.

In yet another embodiment, further including a probe cover, the probe cover including at least one acoustic channel.

In yet another embodiment, the IR thermometer positioning indication includes a graphics display.

In yet another embodiment, the IR thermometer positioning indication includes one or more directionally labeled indicator lamps.

In yet another embodiment, the IR thermometer positioning indication provides an indication of what portion of a tympanic membrane is in a view of the IR detector and the algorithm to convert the IR emission data to a temperature measurement of the area of tissue corrects the temperature measurement based on the indication of what portion of the tympanic membrane is in a view of the IR detector.

In another aspect, the invention features an IR thermometer including an IR sensor configured to generate a temperature signal representative of a temperature of a surface area of tissue. The IR thermometer also includes a microcomputer for converting the temperature signal to the temperature of the surface area of tissue and the microcomputer configured to display the temperature of the surface area of tissue on a display. The microcomputer also includes a guiding means for positioning the IR thermometer for a desired view of the surface area of tissue, wherein the guiding means includes a positioning sensor configured to generate positioning information, the positioning sensor coupled to the microcomputer and an algorithm running on the microcomputer causes a display of IR thermometer positioning information.

In another aspect, the invention features a method for positioning an IR thermometer including the steps of: (a) supplying an IR thermometer including an IR temperature sensor, a guiding means including a positioning sensor, and a microcomputer; (b) receiving at the microcomputer an IR temperature signal from the IR temperature sensor and a positioning signal from the positioning sensor; (c) calculating using the microcomputer an indication of a position of a present view of the IR thermometer with respect to a desired view of a desired area of tissue; (d) indicating a direction to move the position of the IR thermometer towards an improved view of the desired area of tissue; (e) repeating steps (c) and (d) until the IR temperature sensor substantially views the desired area of tissue; and (f) displaying a temperature substantially indicative of a temperature of the desired area of tissue based on the IR temperature signal.

In one embodiment, the step of indicating a direction includes the step indicating a direction to move the position of the IR thermometer towards an improved view of the desired area of tissue, wherein the desired area of tissue is a tympanic membrane.

In another embodiment, the method further includes between step (e) and step (f), the step of: calculating by an algorithm running on the microcomputer a portion of the tympanic membrane in a field of view of the IR temperature sensor and wherein the step of displaying a temperature includes the step of displaying a temperature substantially indicative of a temperature of the desired area of tissue based on the IR temperature signal and the portion of the tympanic membrane in a field of view of the IR temperature sensor.

BRIEF DESCRIPTION OF THE DRAWINGS

For a further understanding of these and objects of the invention, reference will be made to the following detailed description of the invention which is to be read in connection with the accompanying drawing, where:

FIG. 4A shows an IR thermometer having optical ranging;

FIG. 4B shows an IR thermometer including a separate optical receiver for optical ranging;

FIG. 6A shows a narrow optical ranging footprint;

FIG. 6B shows a wider optical ranging footprint than shown in FIG. 6A;

FIG. 7A illustrates an obstruction in an auditory canal;

FIG. 7B shows an exemplary 2D displayed image of the auditory canal and obstruction of FIG. 7A;

FIG. 7C shows an exemplary display having a graphical representation of the location of an obstruction;

FIG. 8B shows an exemplary block diagram of an IR thermometer with acoustic ranging using a separate acoustic transmitter and receiver;

FIG. 8C shows an exemplary block diagram of an IR thermometer with acoustic ranging using a common acoustic transmitter and receiver;

The drawings are not necessarily to scale, emphasis instead generally being placed upon illustrating the principles of the invention. In the drawings, like numerals are used to indicate like parts throughout the various views.

DETAILED DESCRIPTION OF THE INVENTION

The invention pertains to an inventive IR thermometer having a probe cover using features to help an operator position the IR thermometer in a person's auditory canal for a most optimal view of their tympanic membrane. There are several embodiments of the inventive IR thermometer including guiding means that can be roughly divided into optical solutions using optical guiding means based on various optical positioning sensor means, as described in PART I, and acoustical solutions using acoustic guiding means based on various acoustic positioning sensor means, as described in PART II.

Figure 1A:
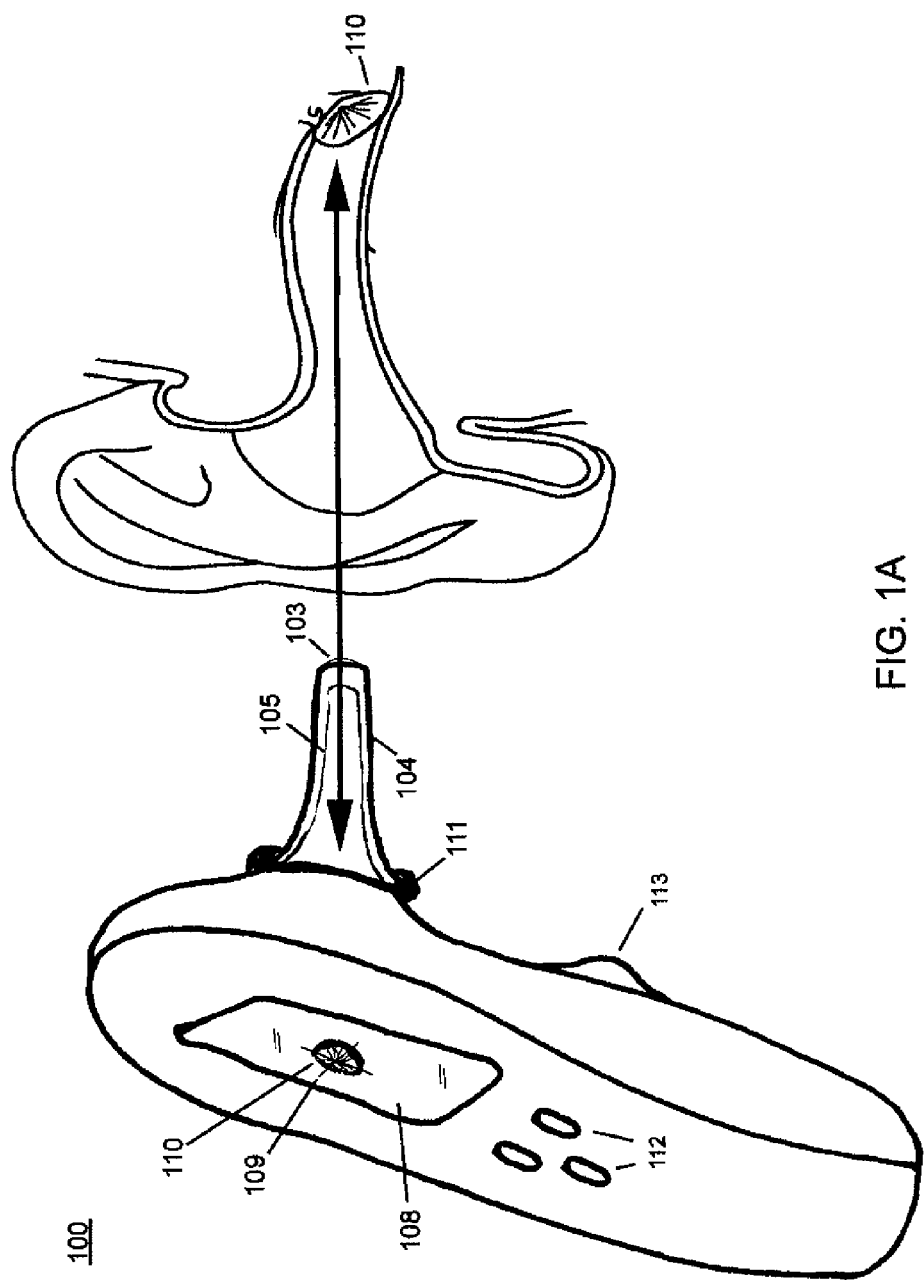
FIG. 1A shows an exemplary embodiment of an inventive optically guided IR Thermometer using a probe cover.

Part I, Optically Assisted IR Thermometer Positioning:

FIG. 1A shows an optically guided IR Thermometer 100 using an exemplary embodiment of an inventive probe cover 104. An optical image of the view through probe cover 104 can be seen on display 108 of IR Thermometer 100. The image presented on display 108 can assist an operator to best position the probe of IR Thermometer 100 in a person's auditory canal, such as by varying the angle of insertion into the auditory canal for an optimal field of view to a person's tympanic membrane 110.

Figure 1B:
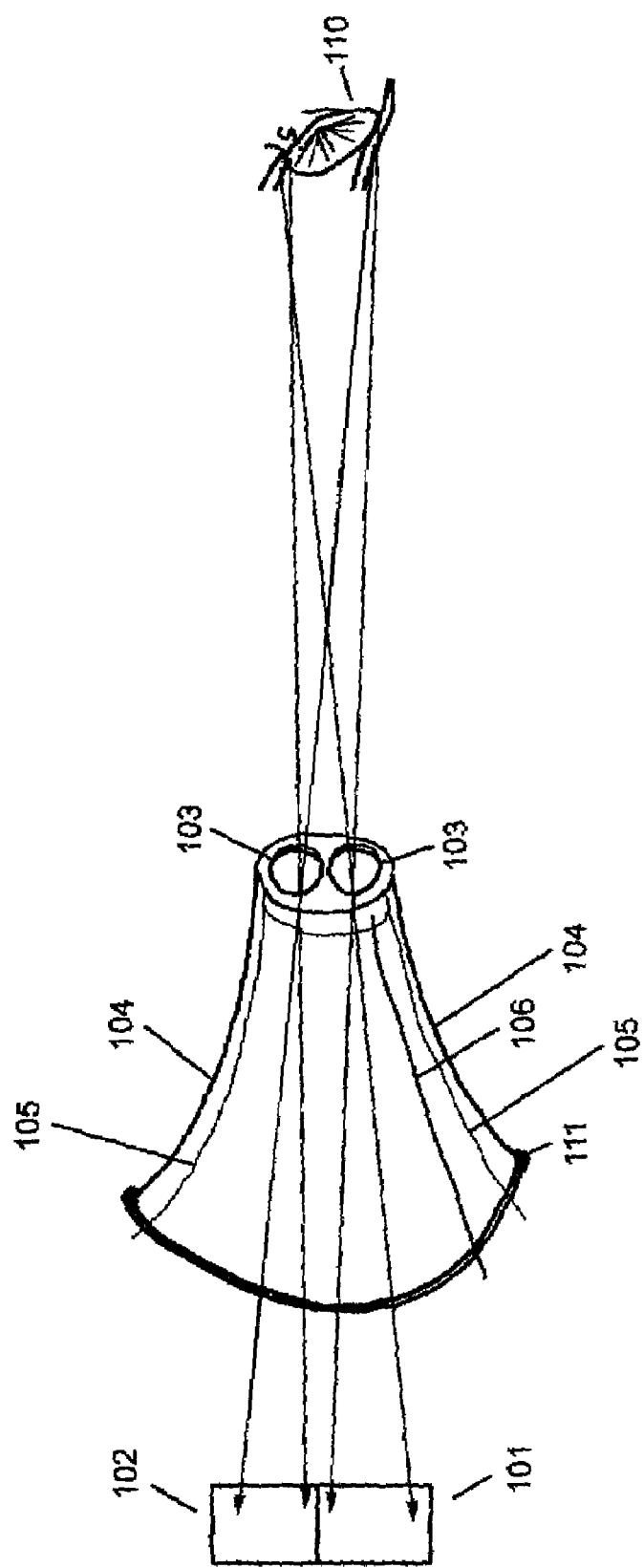
FIG. 1B shows an optically guided IR Thermometer using an exemplary embodiment of an inventive probe cover.

OPTICAL IMAGING: As shown in the exemplary embodiment of FIG. 1B, optical imager 102 can have a view through one or more lenses 103 in probe cover 104. While, in the exemplary embodiment of FIG. 1B, probe cover 103 is shown with two lenses 103, in other embodiments, a single lens or a flat transparent window can be used. Also, there can be additional optical components, typically additional lenses, to focus an image, such as of a tympanic membrane 110, on either or both of optical imager 102 or IR detector 101. IR detector 101 can be situated within or adjacent to tapered conical section probe housing 105 such that IR detector 101 receives IR light from substantially the same field of view as optical imager 102. Probe cover 104 can be a disposable probe cover that fits over a tapered conical section probe housing 105. Disposable probe covers are generally used for hygienic reasons to prevent cross contamination by the spread of pathogens, such as, bacteria or infectious diseases.

Cross-hairs 109 (FIG. 1A) can further assist an operator to optimally position an IR thermometer 100. IR detector 101, optical imager 102, and one or more lenses 103 can be configured such that when the image of the viewable portion of tympanic membrane 110 is substantially centered under cross-hairs 109, IR detector 101 is also measuring the temperature of substantially the same area as being viewed on display 108. Cross-hairs 109 can either be inscribed on or in the surface of display 108, or cross-hairs 109 can be created by software and displayed as part of the image. Illumination of the auditory canal, to facilitate imaging and display of an image on display 108 can be provided, for example, by an optical fiber 106 disposed in the tapered conical section probe housing 105.

Probe cover 104, as well as any of the other probe covers described herein, can also include a probe cover locking mechanism 111 to affix probe cover 104 over probe housing 105 and to the base of probe housing 105 or otherwise to the body of thermometer 100. Such probe cover locking mechanisms have been described in detail in U.S. Pat. No. 6,022,140 to Fraden, et al. and in U.S. Patent Application No. 20050027168, "Otoscopic tip element and related method of use", owned by the Welch Allyn Corporation, and both the '140 patent and the '168 application are incorporated herein by reference in their entirety.

Figure 2:
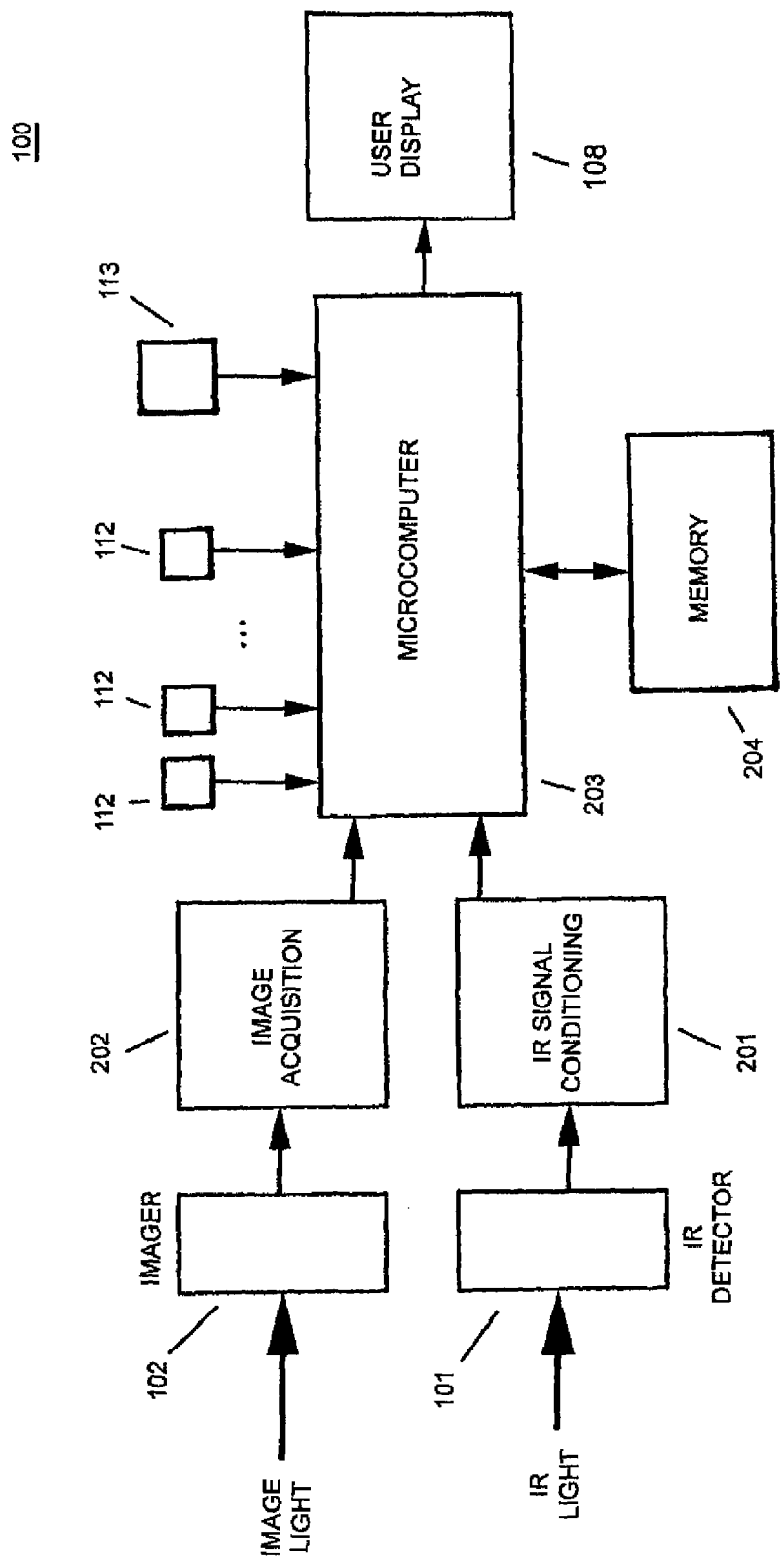
FIG. 2 shows a block diagram of one embodiment of an optically guided IR Thermometer with imaging features.

FIG. 2 shows a block diagram of one embodiment of an IR thermometer 100 suitable for use with inventive probe cover 104. Light from a view inside of the auditory canal can be registered by imager 102. Image acquisition block 202 converts received images into a digital image that can be displayed on user display 108. It is unimportant whether the imager 102 and image acquisition block 202 are separate physical assemblies or present as one physical packaged component or assembly. IR detector 101 can receive IR wavelength light from a field of view within the auditory canal. IR signal conditioning block 201 can provide any electrical biasing, filtering, offsets or gains suitable for a particular model of IR detector 101. It is unimportant whether the IR detector 101 and IR signal conditioning block 201 are separate physical assemblies or present as one physical packaged component or assembly. Microcomputer 203 can receive images from image acquisition block 202 and/or IR signal conditioning block 201. Software, typically firmware, running on microcomputer 203 can convert the signals from IR signal conditioning block 201 into a displayed temperature reading in degree Fahrenheit or degrees Celsius. User operated buttons 112 in conjunction with software running microcomputer 203 can be configured to set various modes of operation of IR thermometer 100 as well as to call for and select configuration and operational menus. A button 113 can be shaped and/or colored differently than buttons 112 and serve as a manually operated trigger to take a temperature measurement, as shown in the exemplary embodiment of FIG. 1A. Typically memory for storing software code as well as data can be present on microcomputer 203 and/or stored on a separate dedicated memory element 204. It is also understood that any analog to digital converters (ADC) used to convert the IR image to a digital signal can either be included within the package of an IR detector 101, as a separate ADC, or can be included within microcomputer 203. Typically, but not necessarily, any ADCs associated with optical image capture can be situated within an image acquisition block 202.

Figure 3A:
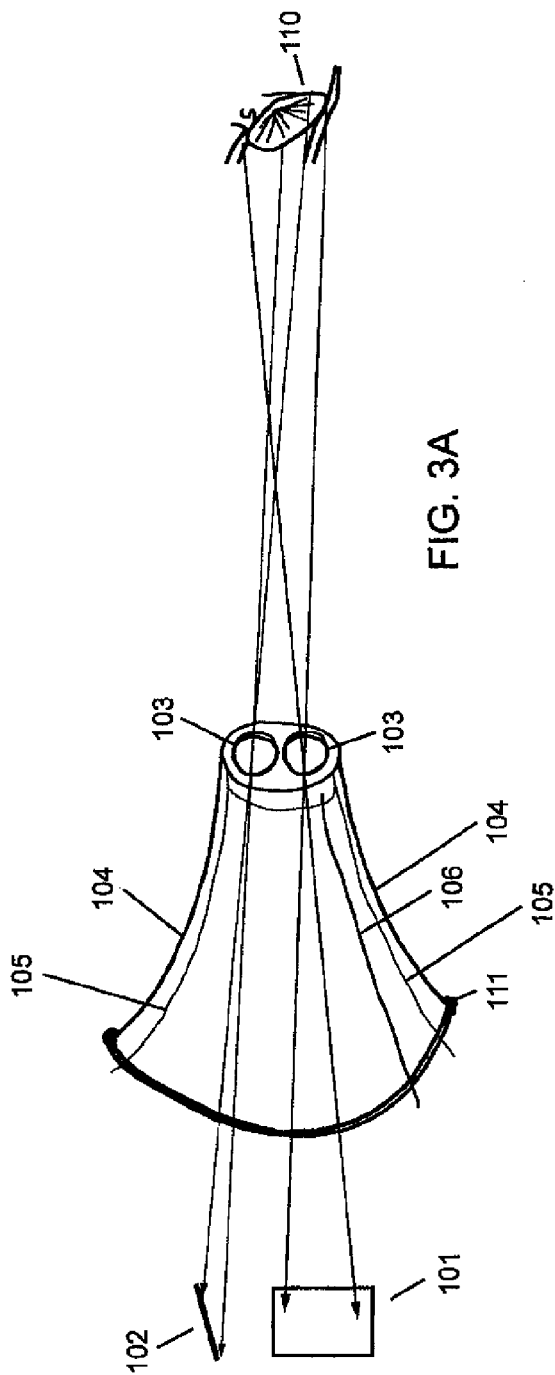
FIG. 3A shows one embodiment of an optically guided IR Thermometer using a probe cover and 1D imaging.
Figure 3B:
FIG. 3B is an illustration of an exemplary 1D image display.
Figure 3C:
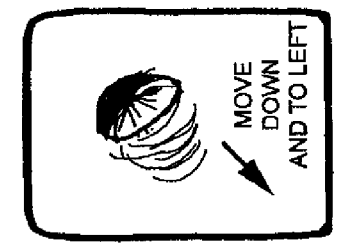
FIG. 3C is an illustration of an exemplary directional guidance screen.

As shown in FIG. 3A, an optical imager 102 can also be a linear (1D) imager. A 1D imager can be used to reduce the cost of an IR Thermometer 100 as compared to an embodiment using a 2D imager. In one embodiment using a 1D imager, as illustrated by FIG. 3B, a linear image of the interior of an auditory canal can be presented to the operator to aid in guiding IR Thermometer 100 into an optimal measuring orientation. In another embodiment using a linear imager, as shown in FIG. 3C, an algorithm running on a computer 203 can be used to offer the operator directional positioning suggestions on display 108, based on an array of image data read from a linear imager 102. For example, as shown in FIG. 3B, where the image suggests the IR detector 101 is viewing the left side of the ear canal, a display icon (FIG. 3C) or lamp indicator can assist the operator by suggesting moving the IR viewing area to the right. In the embodiments of FIG. 3C, the linear image of FIG. 3B can also be presented on a display 108 in addition to the direction indicator.

Since a 1D imager is limited to providing positioning information in a single direction, e.g. left-right or up-down; In another embodiment, two 1D imagers oriented substantially perpendicular to each other can provide more positioning information. The two perpendicular 1D imagers can be in a "crossed" arrangement or situated adjacent to one another. A pair of 1D imagers, such as two substantially orthogonal 1D imagers, can provide a relative position of the tympanic membrane. Both 1D images can be directly displayed on display 108 and/or an algorithm running on microcomputer 203 can analyze the 1D images to determine the position of the tympanic membrane 110 such as by intensity and/or color variations.

While an operator could be trained to properly position an IR thermometer 100 by directly viewing images from one or more 1D imagers on a display 108, a displayed picture can provide a more intuitive positioning guide. In another embodiment having one or more 1D or 2D imagers, it is believed that the operator can be shown pre-stored or "generic" 2D images or pictures representative of what an IR thermometer is viewing as determined using a positioning sensor of a guidance means. For example, there can be a plurality of various generic views of the human auditory canal and tympanic membrane pre-stored in memory on IR thermometer 100 for display on display 108. Such views can be "text book views" or actual images of views of the human ear. Such views can include images of the ear, including the auditory canal and tympanic membrane from different probe positions.

Figure 3D:
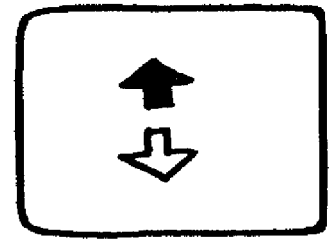
FIG. 3D is an illustration of an exemplary pre-stored image and positioning guidance screen.
Figure 3E:
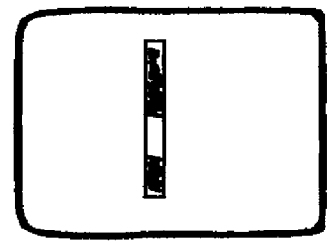
FIG. 3E is an illustration of an exemplary IR thermometer probe position corresponding to FIG. 3D.

For example, as shown in FIG. 3E, an IR thermometer probe 100 is illustrated as directed, from an operator's perspective, slightly to the right and slightly up. It is believed that an algorithm running on microcomputer 203 can determine from the location of intensity and/or color variations as viewed by one or more imagers, what direction the IR thermometer 100 probe should be moved to bring the image of the tympanic membrane near center so that the IR detector 101 can be oriented for a better view of tympanic membrane 110. As shown in FIG. 3D, the microcomputer can choose and display on display 108 a pre-stored picture that best represents how the operator should re-orient the IR thermometer 100 for a more optimal view of the person's tympanic membrane 110. We note that displaying generic images, such as pre-stored pictures or line drawings of generic pictures to indicate IR Thermometer 100 orientation can be used in any embodiment where orientation information is available including embodiments using 2D imagers, and is not limited to the linear imaging example.

OPTICAL RANGING: Another approach believed useful for determining the orientation of an IR Thermometer 100, such as for viewing an ear canal, can be based on optical ranging. Optical ranging technology for close up views is available, for example, as has been used for both manual and auto focus lenses as associated with "macro" lenses in conventional photography. In a very basic embodiment, split images can be present in an optical view finder as have been used on early single lens reflex (SLR) cameras. Focusing optics can be included in an IR thermometer 100 such that when the tympanic membrane 110 is within a typical anticipated distance, the split images come together.

FIG. 4A shows a more sophisticated embodiment for optical ranging using an IR lamp 401, such as an IR light emitting diode (LED). Optical imager 101 receives the IR light reflected from the tympanic membrane 110 when thermometer 100 is properly oriented, or from the walls of the auditory canal if incorrectly positioned. Conventional optics can be used, including a lens 103 in a probe cover 104, such that as the position changes, the image from IR lamp 401 moves across optical imager 101. An algorithm running on microcomputer 203 can determine the orientation of the IR thermometer 101 by analyzing, for example, light and dark areas on either a 1D or 2D imager caused by IR lamp 401 and the pre-defined optics path between IR lamp 401 and imager 101. Note that this method is different from a previously discussed method of looking for the warmest spot in an image of the tympanic membrane 110 and surrounding auditory canal. In the optical ranging embodiment of FIG. 4A, the light area being analyzed is primarily reflected IR light from IR lamp 401. In embodiments such as shown in FIG. 4A, where the optical imager 101 serves dual functions of positioning guidance and temperature measurement, there can be time multiplexing such that for a period of time, optical imager 101 is dedicated to positioning tasks, generally followed by a time where IR lamp 401 is switched off and optical imager 101 is used for temperature measurements.

In a similar optical ranging embodiment shown in FIG. 4B, a separate optical receiver 402 can be configured to receive light from IR lamp 401. In embodiments where the ranging lamp and detector do not use optical imager 101 as part of the ranging system, lamp 401 need not necessarily be an IR lamp and can have any useable light wavelength. Detector 402 can be a point detector, such as a photo diode, for a single point guiding arrangement, or can be a 1D or 2D imager sensitive to a wavelength suitable to receive light emitted by lamp 401.

While the embodiments of FIG. 4A and FIG. 4B have been discussed as using optical elements, typically one or more lenses that move the location of light and dark areas of illumination on detectors or imagers 101 or 402, other optical ranging techniques can be used. For example, it is also believed that time of travel of a pulse of light from lamp 401 to a detector or imager can be measured to yield a distance using RADAR principles. Longer pulse travel times from lamp 401 to a detector or imager 101 or 402 can indicate a more desirable path through the auditory canal to the tympanic membrane 110.

Any of the aforementioned range determinations can be also be used to determine the amount (percentage) of the tympanic membrane in the field of view of the IR temperature sensor. The temperature read by the IR thermometer (based on one or more measured values from the temperature sensor) can then be adjusted to a value more indicative of the actual tympanic temperature based on the determination of what percentage of the tympanic membrane is in the field of view.

In still other embodiments it is believed that light from more than one lamp 401 can be directed in differing forward directions into the auditory canal. Here reflections from each lamp 401 can be analyzed by an algorithm running on microcomputer 203. With ranging information from several forward directions, guidance can be given, for example on a display 108, showing what direction to move the IR thermometer 100 to achieve a more optimal view of the tympanic membrane. Light from lamps 401 can be more narrowly collimated and focused in this case by a combination of masking, collimating lenses, and/or optical fibers. Lamps 401 can also be a laser, such as a solid state laser. In embodiments using multiple lamps 401 several techniques can be used to distinguish the ranging measurement associated with each lamp 401. In one embodiment, each light path from lamp 401 to a respective detector or imager can be isolated from each other for minimal cross-talk. In another embodiment, each lamp 401 can emit a different wavelength of light. In yet another embodiment, ranging measurements can be obtained using a plurality of lamps where the illumination of each lamp 401 can be staggered in time, so that each ranging measurement can be made at a different time.

As previously noted, where an optical ranging or guiding system uses a common imager 101, the time for ranging and guiding and IR thermometry can be split to avoid corrupting the temperature measurement with light from one or more lamps 401. In embodiments where one or more separate detectors or imagers 402 are used for guidance, and are operated at a non-IR wavelength, there can be less concern that light from a ranging or positioning guidance system will cause an error in the IR thermometry measurement by direct illumination. Another source of error, however, can be caused by an optical ranging or positioning system as caused by direct or indirect heating the auditory canal. In such cases it can be desirable to pulse one or more lamps 401 at a relatively low duty cycle.

While various optical embodiments have been illustrated with relatively straight ear canals, actual ear canals can have a variety of paths and variation in opening diameter along the axis from the outer surface of the ear to the tympanic membrane. Some of these paths can be relatively straight and others tortuous. It is contemplated that at least in some embodiments including a microcomputer, algorithms can be used to detect unusual physiological structure in an ear canal and to adjust accordingly directional guidance to an operator of an IR Thermometer 100 and/or to adjust the displayed temperature to a value more indicative of the actual tympanic temperature measurement if it is determined that the field of view includes none of, or only a portion of, the tympanic membrane.

Figure 5A:
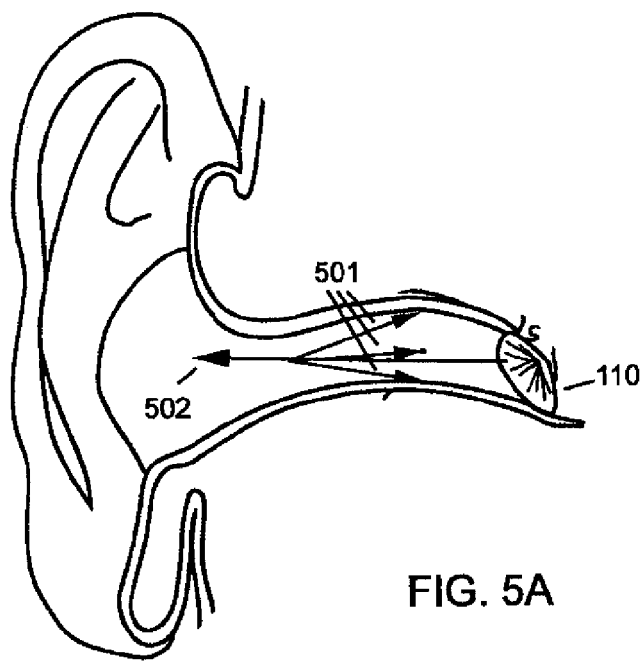
FIG. 5A shows an illustration of multiple point optical ranging in the auditory canal of a human ear.
Figure 5B:
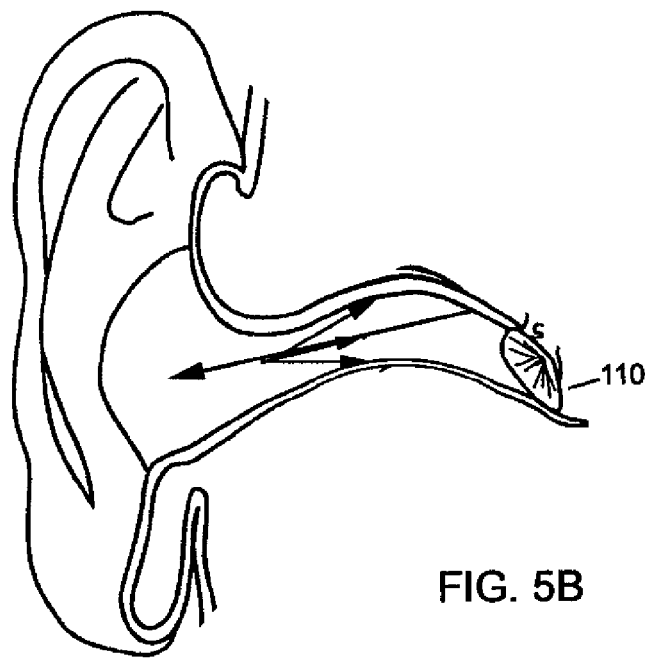
FIG. 5B shows an illustration of multiple point optical ranging with an IR thermometer at a different orientation than shown in FIG. 5A.

FIGS. 5A, 5B, show two views of auditory canals and ranging optical rays 501 associated with three ranging sensors. FIG. 5A illustrates multiple point optical ranging in a human ear. Roughly equal ranges in FIG. 5A from all three range sensors yield a substantially proper view of the IR radiation 502 from tympanic membrane 110. For the more tortuous auditory canal illustrated in FIG. 5B, roughly equal range determinations from three range sensors position can cause the IR detector to be incorrectly positioned for a view above tympanic membrane 110, resulting in an IR measurement of the auditory canal. In such cases using three or more range sensors, an algorithm running on microcomputer 203 can recognize a more indirect path and to rely on two of the three sensors alone or in combination with processing temperature information as the IR thermometer is moved to seek a proper alignment.

Figure 5C:
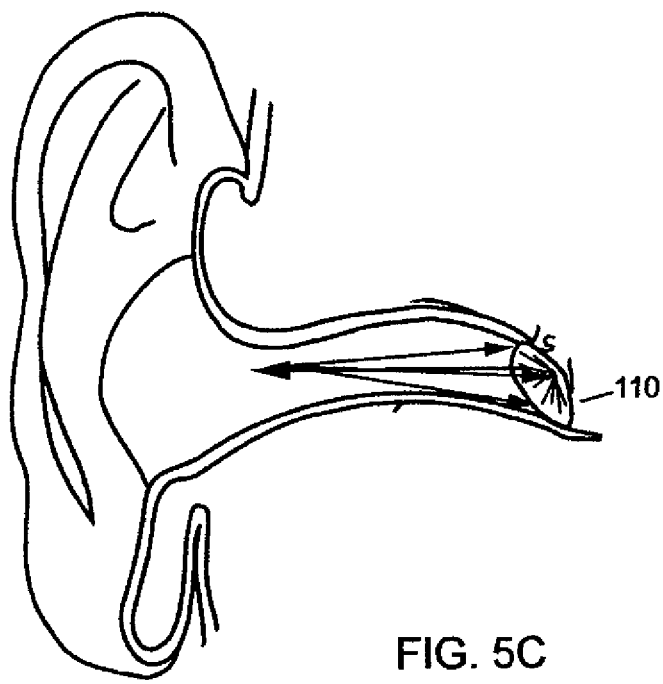
FIG. 5C shows an illustration of multiple point optical ranging using a narrower cone of ranging than shown in FIG. 5B.
Figure 5D:
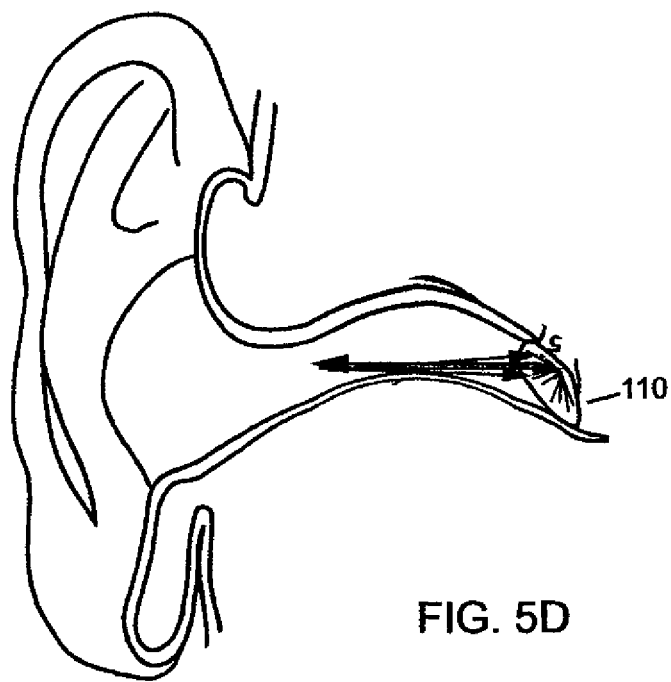
FIG. 5D shows an illustration of multiple point optical ranging using a narrower cone of ranging than shown in FIG. 5C.

Another approach for improving the positioning of an IR thermometer 100 using multiple ranging is shown in FIG. 5C and FIG. 5D. Here, it is believed that the "cone" of ranging can be narrowed for more direct ranging measurements of the tympanic membrane 110. In the tortuous canal depicted in FIG. 5D, a relatively narrow cone of ranging can solve the problem of indirect ranging that was illustrated in FIG. 5B.

The divergence of each optical ranging ray 501 in FIG. 5A to FIG. 5D can also range from narrow to wider in a reflection foot print 601 as shown in FIG. 6A and FIG. 6B. The divergence of each ranging illumination ray can be accomplished by a collimating mask and or collimating optics. The size of the corresponding circular or elliptical footprint 601 can be set accordingly.

FIG. 7A illustrates a view of an auditory canal having an obstruction 701. Obstruction 701 can be a foreign body or material such as an insect, debris, blood, or cerumen (earwax), or a growth or other pathology including infection or inflammation. As shown in FIG. 7A, at least one of the ranging views is likely to intercept an obstruction 701. An algorithm running in software, such as on a microcomputer 203, can recognize some shorter ranges as obstructions. For example, where one or more ranging measurements are very different from each other, a partial obstruction is a possibility. On detection of an obstruction 701, it is believed that a version of an IR thermometer 100 using optical imaging capability can display an image of the auditory canal including obstruction 701 as shown in FIG. 7B. More likely, an IR thermometer 100, such as one using optical ranging, might not include a full 2D imager. In such cases, a display such as shown in FIG. 7B can be presented based on pre-stored images of obstructions. A plurality of generic images of for example, obstructions of different sizes and/or obstructions at different locations in an auditory canal can be pre-stored. Depending on which range is short, the most suitable pre-stored image showing an obstruction nearest to the predicted location can be shown. Alternatively, a single bar graph can be shown on display 108, for example indicating the extent of the walls of the auditory canal by markers 704, and/or showing the predicted or measured location obstruction 701, such as by the "X" marker 702 and/or an inverted "V" 703. With a suitable number of range sensors or a 2D imaging range sensor, there can also be a crossed bar graph giving up-down and right-left location of an obstruction 701 (not shown in FIG. 7C).

It is noted that while several of the previous optical embodiments were illustrated with a probe cover having two lenses 103, many of these embodiments can function equally well with one common lens 103. In other embodiments, particularly those using multiple lamps 401, it can be advantageous to use a plurality of lenses 103. In still other optical embodiments lens 103 can include one or more Fresnel lens. Also, for simplicity, only lenses 103 have been shown in the drawings. It will be understood by those skilled in the art that many of the embodiments described can include additional lenses and masks for collimation, focusing, and establishing viewing apertures.

Part II, Acoustically Assisted IR Thermometer Positioning:

One problem associated with optically assisted positioning is that the illumination of the ear canal associated with most imaging and/or optical ranging can cause errors in the IR temperature measurement. A first source of error can be caused by visible light illumination. Errors caused by visible light can be made relatively small, however, since visible light can be either far outside of the sensitivity of an IR sensor and/or visible light can be filtered by a filter that substantially passes only IR light situated in the light path to an IR detector 101 or IR imager. A second source of error caused by direct heating of the ear canal by the source of visible light illumination can be more problematic. In some embodiments, it can be difficult to determine how much temperature elevation of the ear canal and/or tympanic membrane might be caused by a source of visible illumination in an IR Thermometer 100 using an optically assisted positioning technique. It is believed that a solution is to use audio or acoustic imaging or ranging for IR Thermometer assisted positioning. We now describe several embodiments of IR Thermometers using acoustically assisted positioning.

Figure 8A:
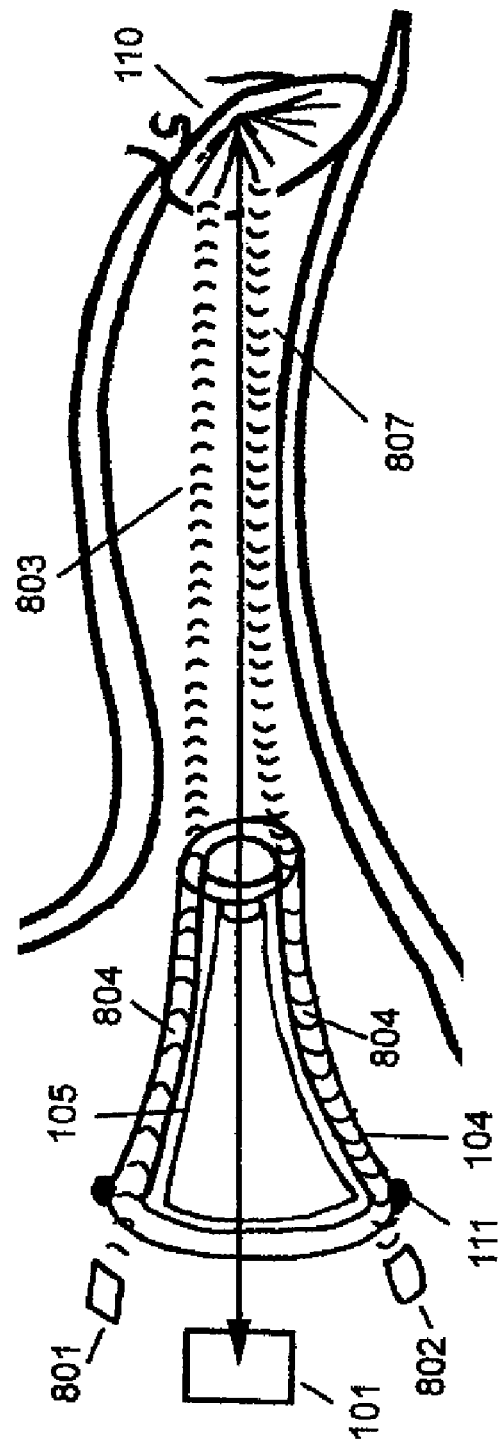
FIG. 8A illustrates a probe cover for use with an IR thermometer using acoustic ranging.

ACOUSTIC RANGING: In one exemplary embodiment shown in FIG. 8A, it is believed that a range to a surface area in an ear canal can be determined by acoustic transducers, such as piezo elements, using SONAR or other acoustic ranging techniques including phase and/or wave-shape comparisons between transmitted and received acoustic signals. In the embodiment of FIG. 8A, an acoustic transmitter 801, such as a piezoelectric element, sends audio, typically as an acoustic pulse, out through an acoustic channel 804 in a probe cover 104. One or more acoustic pulses 803 traverse the air space in the auditory canal and bounce off of the tympanic membrane 110. Each reflected acoustic pulse can be received by acoustic receiver 802 via acoustic channel 804 in probe cover 104. Acoustic ranging can be performed using any acoustic wave shapes, pulses, and/or acoustic frequencies suitable for acoustic ranging applications. Such frequencies typically range from audio to ultrasonic frequencies.

FIG. 8B shows a block diagram of exemplary electronics believed to be suitable to provide a range measurement using an acoustic transmitter 801 and an acoustic receiver 802. An algorithm running on microcomputer 203 can determine when an acoustic range measurement is to be made, such as following depression of a temperature measure button (e.g. button 113, FIG. 1A). Acoustic pulses can be generated in an electrical form by an acoustic signal and ranging circuit 811. Outgoing acoustic pulses can be amplified as needed by amplifier 810 and transmitted out of an acoustic channel 804 of probe cover 104 (FIG. 8A). Returning acoustic signals 803 (FIG. 8A) can be received by acoustic receiver 802 and further processed by acoustic signal and ranging circuit 811. A range value can be returned by acoustic signal and ranging circuit 811 to microcomputer 203. It is unimportant whether the actual range determination is made in hardware, such as by an acoustic signal and ranging circuit 811 or in a microcomputer 203 such as in an embodiment where transmit and receive times or phases or phase differences are conveyed directly to microcomputer 203 for a range determination. Based on the range determination, an operator can be guided by software running on a microcomputer 203 towards an optimal view of the tympanic membrane 110 by IR detector 101. For example, in the single range embodiment of FIG. 8A, algorithms accomplished in software running on microcomputer 203 can include typical expected depths to the tympanic membrane, and shorter depth readings representative of more reflection from closer in acoustic canal walls. In the embodiment of FIG. 8A, an operator can slightly reposition the IR thermometer 100 until an acceptable depth range is achieved as can be indicated by an icon, message, graphic, or text on a display screen 108 and/or by an indicator lamp. Also range information can be used to adjust the displayed temperature to a value more indicative of the actual tympanic temperature measurement if it is determined that the field of view includes none of, or only a portion of, the tympanic membrane.

In a similar embodiment of acoustically assisted IR thermometer positioning as shown in FIG. 8C, it is believed that an acoustic transceiver 823 can combine the transmit and receive functions of acoustic transmitter 801 and acoustic receiver 802 into a single acoustic transducer.

Figure 8D:
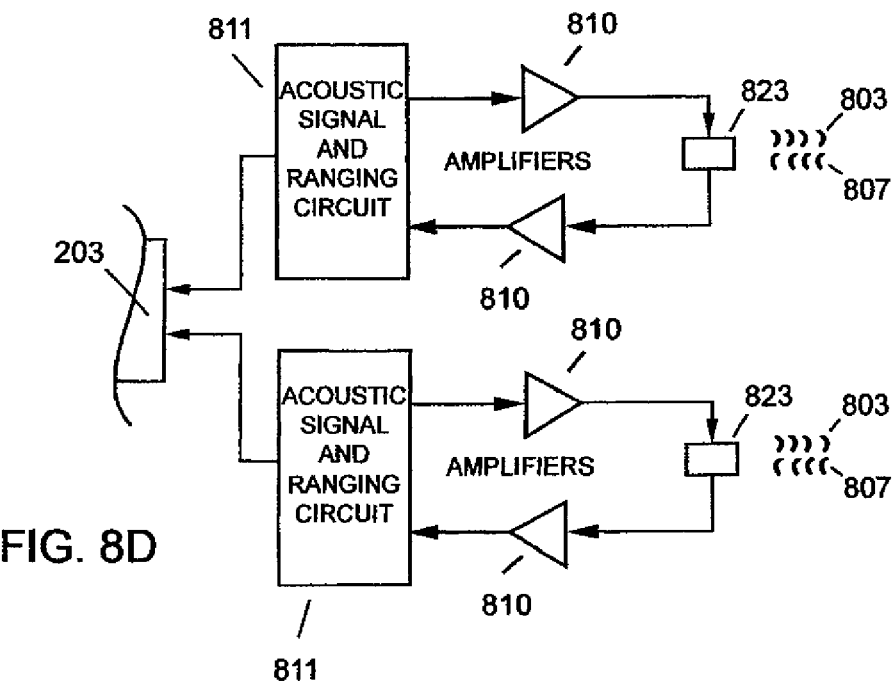
FIG. 8D shows an exemplary block diagram of an IR thermometer with multiple acoustic ranging using common acoustic transmitters and receivers.
Figure 8E:
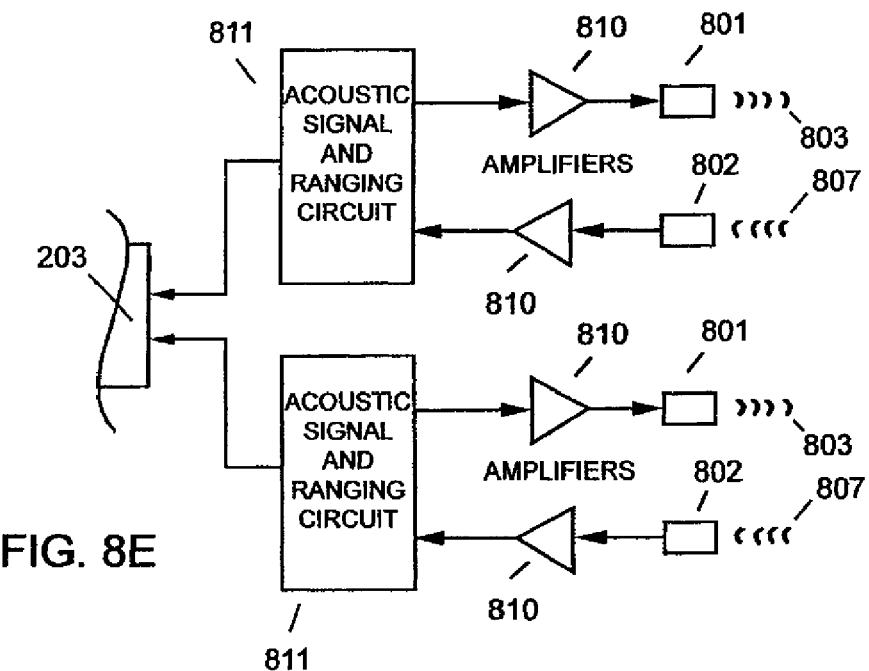
FIG. 8E shows an exemplary block diagram of an IR thermometer with multiple acoustic ranging using separate acoustic transmitters and receivers.

It is also believed that other embodiments of acoustically assisted IR thermometer positioning can use two or more range measurements for providing directional guidance such as right-left or up-down. FIG. 8D shows an exemplary block diagram of an IR thermometer with multiple acoustic ranging using common acoustic transmitters and receivers. The exemplary block diagram of FIG. 8E shows an acoustic ranging embodiment using two sets of piezo range sensors 801, 802, amplifiers 810, and acoustic signal and ranging circuit 811 for two range measurements. Acoustic signal and ranging circuit 811 can control the transmission of acoustic pulses 803 and measure the time difference between transmission of acoustic pulses 803 and reception of reflected acoustic signals 807. It is believed that in other embodiments, transmission of pulses 803 and/or time difference calculations might be performed directly in microcomputer 203.

Figure 8F:
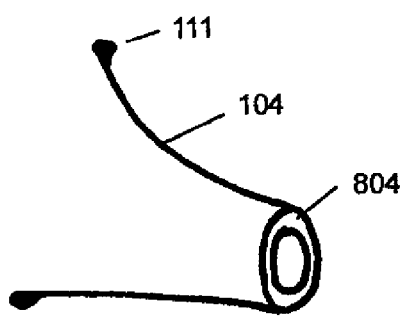
FIG. 8F shows an exemplary probe cover having an cylindrically symmetric conical form acoustic channel.
Figure 8G:
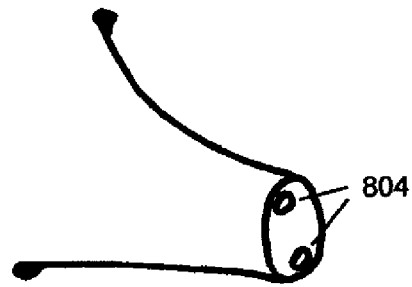
FIG. 8G shows an exemplary probe cover having two acoustic channels.
Figure 8H:
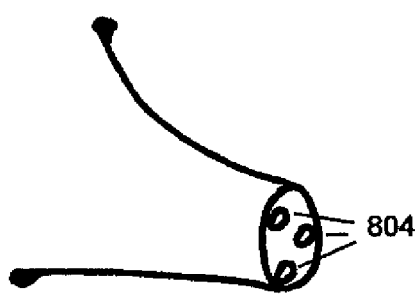
FIG. 8H shows an exemplary probe cover having three acoustic channels.
Figure 8I:
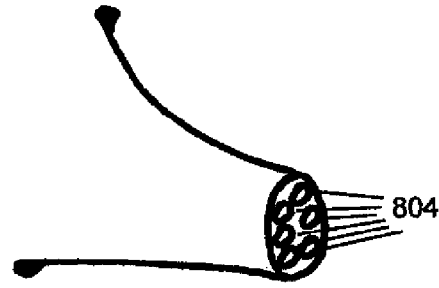
FIG. 8I shows an exemplary probe cover having six acoustic channels.

FIG. 8F shows a probe cover 104 having one cylindrically symmetric acoustic channel 804. In other embodiments, such as shown in FIG. 8B, where there is a separate acoustic transmitter 801 and acoustic receiver 802, there can also be dedicated acoustic channels 804 for transmit and receive as illustrated by the probe cover 104 of FIG. 8G. FIG. 8H shows an exemplary probe cover 104 having three shared function transmit and receive acoustic channels 804, and FIG. 8I shows a three range embodiment having separate transmit and receive acoustic channels 804. The arrangement of transmit and receive acoustic channels, such as the distribution and location of transmit acoustic channels corresponding to their respective receive channels can be varied in multiple ranging embodiments using separate transmitters 802 and receivers 803. Also, the shape of each acoustic channel 804 can be other than round or oval and can also be square or rectangular and/or partially follow the contours of probe cover 104.

Figure 9A:
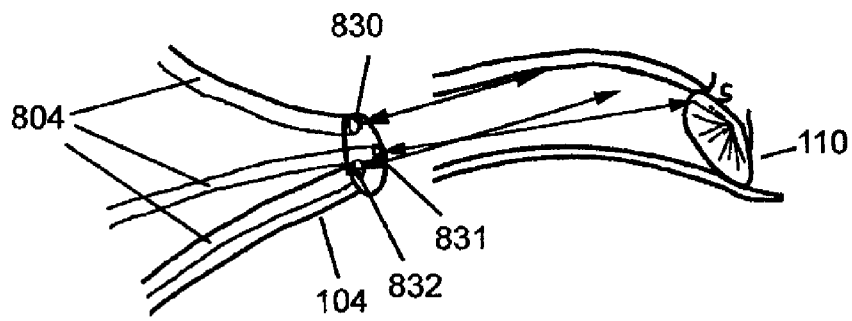
FIG. 9A shows an illustration of a three acoustic channel probe cover being used to range distances in an auditory canal.
Figure 9B:
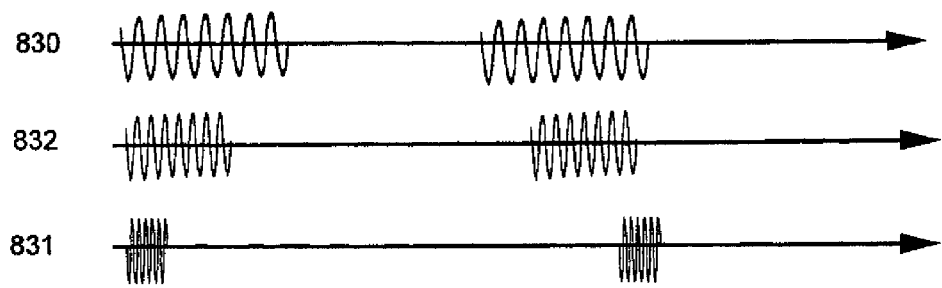
FIG. 9B shows a graph of three acoustic signals having three different acoustic frequencies.
Figure 9C:
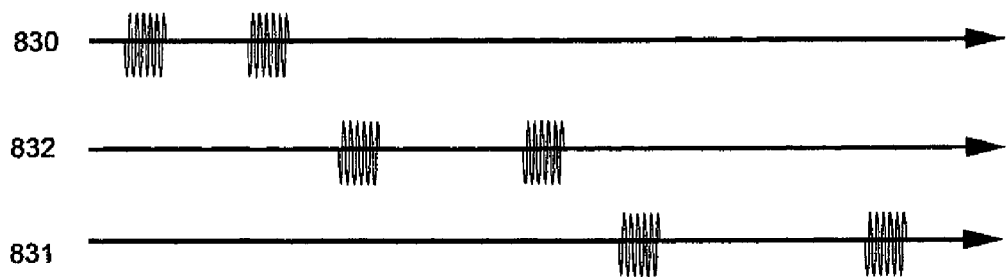
FIG. 9C shows a graph of three acoustic signals separated in time.

FIG. 9A shows an exemplary acoustically assisted positioning embodiment of an IR thermometer 100 in a partial view from a probe cover 104 forward towards the tympanic membrane 110. In FIG. 9A, there are three channels of acoustic ranging using three acoustic transceivers 823 (not shown in FIG. 9A) in a three channel embodiment similar to the two channel block diagram of FIG. 8D. FIG. 9B and FIG. 9C show two exemplary techniques for separating and distinguishing each of the three acoustic range measurements 830, 831, and 832. For example, in FIG. 9B, three acoustic frequencies are used to separate the individual range measurements. Analog and/or digital filtering can be used in any of the transmit and/or receive blocks to enhance the acoustic channel separation and isolation between channels. Additional digital filtering can be done in software running on a microcomputer such as microcomputer 203. In FIG. 9C, a time multiplexed scheme is used where each acoustic range can be taken staggered in time from the others. Computer analysis of the image, such as can be performed by a microcomputer, can be used to adjust the displayed temperature to a value more indicative of the actual tympanic temperature measurement if it is determined that the field of view includes none of, or only a portion of, the tympanic membrane.

We also note that while the exemplary embodiments having multiple transmissions and receptions of acoustic pulses as illustrated in FIG. 9A to FIG. 9C use time difference measurements, it is believed that other embodiments could use multiple transmissions and receptions of acoustic pulses, such as by time multiplexing or with different frequencies, can make use of other relatively "short range" or small confined space ranging techniques, such as ranging techniques including phase and/or wave-shape comparisons between transmitted and received acoustic signals.

Another acoustic technique that could be useful for developing guidance information includes an acoustic transmitter—receiver pair, a modulated transmitted acoustic signal, and a filtered and rectified received acoustic signal such as described by Ward in U.S. Pat. No. 4,009,707, Automatic acoustic impedance meter, issued Mar. 1, 1977. While Ward was measuring acoustic impedance and compliance, it is contemplated that such techniques could be adaptable as guidance means by, for example, for making depth measurements as an IR thermometer and corresponding acoustic positioning sensors change angle with respect the auditory canal. The '707 patent is incorporated herein by reference in its entirety.

ACOUSTIC IMAGING: In another acoustic embodiment of an image positioning assisted IR thermometer 100, analogous to an ultrasound imager, it is believed that an array of ultrasound elements, acting as an array of transmit-receive pairs, can provide a two dimensional image of the ear canal as viewed through an IR probe cover. In one embodiment of an ultrasound imaging IR thermometer, an operator can view at least a rudimentary two dimensional image of an ear canal, such as on a display 108, while orienting an IR thermometer probe for a best view of tympanic membrane 110 and an optimal temperature measurement.

We define "microcomputer" herein as synonymous with microprocessor, microcontroller, and digital signal processor ("DSP"). It is understood that memory used by the microcomputer, including for example IR thermometer "firmware" can reside in memory physically inside of a microcomputer chip or in memory external to the microcomputer or in a combination of internal and external memory. Similarly, analog signals can be digitized by a stand alone analog to digital converter ("ADC") or one or more ADCs or multiplexed ADC channels can reside within a microcomputer package. It is also understood that field programmable array ("FPGA") chips or application specific integrated circuits ("ASIC") chips can perform microcomputer functions, either in hardware logic, software emulation of a microcomputer, or by a combination of the two. IR thermometers having any of the inventive features described herein can operate entirely on one microcomputer or can include more than one microcomputer.

It can now be seen that a guiding means can be an optical or acoustic system helpful for guiding an IR thermometer into a proper position for a substantially optimal view of a desired area of tissue, such as where the area of tissue of is a tympanic membrane. A positioning sensor includes a sensor or sensor system that can determine a present position of a view of an IR thermometer, so that the guiding means, such as by using a microcomputer, can determine a direction to move the thermometer for a more optimal view of the desired area of tissue where the temperature is to be measured. Positioning sensors as described herein include, but are not limited to, imagers, detectors, acoustic transmitters, receivers, and transceivers.

While the present invention has been particularly shown and described with reference to the preferred mode as illustrated in the drawing, it will be understood by one skilled in the art that various changes in detail may be affected therein without departing from the spirit and scope of the invention as defined by the claims.

We claim:

1. An Infrared (IR) thermometer comprising:
   an IR detector configured to provide an IR emission data representative of a temperature of an area of tissue;
   one or more secondary sensors configured to provide an IR thermometer positioning data; and
   at least one microcomputer coupled to said IR detector, said at least one microcomputer configured to receive said IR emission data from said IR detector and
   said at least one microcomputer running software including an algorithm to convert said IR emission data to a temperature measurement of said area of tissue, and
   said at least one microcomputer also coupled to said one or more secondary sensors, said at least one microcomputer also configured to receive said IR thermometer positioning data from said one or more secondary sensors and
   said at least one microcomputer configured to run an algorithm to convert said IR thermometer positioning data to an IR thermometer positioning indication,
   wherein said IR thermometer positioning indication suggests a direction to move said IR thermometer for a substantially optimal IR detector view of said area of tissue; and
   wherein said at least one microcomputer is further configured to run an algorithm to correct said temperature measurement of said area of tissue to a temperature measurement value more indicative of an actual tympanic temperature based on a determination of what percentage of the tympanic membrane is in the field of view.

2. The IR thermometer of claim 1, wherein said one or more secondary sensors comprise one or more optical sensors.

3. The IR thermometer of claim 1, wherein said one or more secondary sensors comprise one or more acoustic sensors.

4. The IR thermometer of claim 3, wherein said algorithm to convert said IR thermometer positioning data to an IR thermometer positioning indication comprises analyzing said IR thermometer positioning data from said one or more secondary sensors to determine one or more distances based on acoustic ranging.

5. The IR thermometer of claim 4, wherein said acoustic ranging comprises a measurement of time differences between transmitted and received acoustic signals.

6. The IR thermometer of claim 4, wherein said acoustic ranging comprises a range measurement based on phase differences between transmitted and received acoustic signals.

7. The IR thermometer of claim 4, wherein said acoustic ranging comprises a range measurement based on waveshape differences between transmitted and received acoustic signals.

8. The IR thermometer of claim 4, further comprising a probe cover, said probe cover comprising at least one acoustic channel.

9. The IR thermometer of claim 3, wherein said one or more acoustic sensors comprise one or more acoustic receivers and acoustic transmitters.

10. The IR thermometer of claim 3, wherein said one or more acoustic sensors comprise one or more acoustic transceivers.

11. The IR thermometer of claim 2, wherein said algorithm to convert said IR thermometer positioning data to an IR thermometer positioning indication comprises a display of an image of substantially the same field of view of said IR detector.

12. The IR thermometer of claim 11, wherein said image is an actual 1D or 2D image of said area of tissue in a field of view of said IR detector as viewed by an optical imager.

13. The IR thermometer of claim 11, wherein said 1D or 2D image is a pre-stored 2 D image selected by said algorithm as representative of the field of view most likely being viewed by said IR detector.

14. The IR thermometer of claim 2, wherein said one or more optical sensors comprise one or more two dimensional (2D) optical imagers.

15. The IR thermometer of claim 2, wherein said one or more optical sensors comprise one or more one dimensional (1D) optical imagers.

16. The IR thermometer of claim 2, wherein said algorithm to convert said IR thermometer positioning data to an IR thermometer positioning indication comprises analyzing said IR thermometer positioning data from said one or more secondary sensors to determine one or more distances based on optical focus.

17. The IR thermometer of claim 2, wherein said algorithm to convert said IR thermometer positioning data to an IR thermometer positioning indication comprises analyzing said IR thermometer positioning data from said one or more secondary sensors to determine one or more distances based on optical ranging.

18. The IR thermometer of claim 2, further comprising a probe cover, said probe cover comprising at least one optical lens.

19. The IR thermometer of claim 1, wherein said IR thermometer positioning indication comprises a graphics display.

20. The IR thermometer of claim 1, wherein said IR thermometer positioning indication comprises one or more directionally labeled indicator lamps.

21. An Infrared (IR) thermometer comprising:
   an IR detector configured to provide an IR emission data representative of a temperature of an area of tissue;
   one or more secondary sensors configured to provide an IR thermometer positioning data; and
   at least one microcomputer coupled to said IR detector, said at least one microcomputer configured to receive said IR emission data from said IR detector and
   said at least one microcomputer running software including an algorithm to convert said IR emission data to a temperature measurement of said area of tissue, and
   said at least one microcomputer also coupled to said one or more secondary sensors, said at least one microcomputer also configured to receive said IR thermometer positioning data from said one or more secondary sensors and said at least one microcomputer configured to run an algorithm to convert said IR thermometer positioning data to an IR thermometer positioning indication, wherein said IR thermometer positioning indication suggests a direction to move said IR thermometer for a substantially optimal IR detector view of said area of tissue, wherein said IR thermometer positioning indication provides an indication of what portion of a tympanic membrane is in a view of said IR detector and said algorithm to convert said IR emission data to a temperature measurement of said area of tissue corrects said temperature measurement based on said indication of what portion of said tympanic membrane is in a view of said IR detector.

22. A method for positioning an IR thermometer comprising the steps of:
  (a) supplying an IR thermometer including an IR temperature sensor, a guiding means including a positioning sensor, and a microcomputer;
  (b) receiving at said microcomputer an IR temperature signal from said IR temperature sensor and a positioning signal from said positioning sensor;
  (c) calculating using said microcomputer an indication of a position of a present view of said IR thermometer with respect to a desired view of a desired area of tissue;
  (d) indicating a direction to move said position of said IR thermometer towards an improved view of said desired area of tissue;
  (e) repeating steps (c) and (d) until said IR temperature sensor substantially views said desired area of tissue; and
  (f) displaying a temperature substantially indicative of a temperature of said desired area of tissue based on said IR temperature signal.

23. The method of claim 22, wherein the step of indicating a direction comprises the step indicating a direction to move said position of said IR thermometer towards an improved view of said desired area of tissue, wherein said desired area of tissue is a tympanic membrane.

24. The method of claim 23, further comprising between step (e) and step (f), the step of: calculating by an algorithm running on said microcomputer a portion of the tympanic membrane in a field of view of said IR temperature sensor and wherein said step of displaying a temperature comprises the step of displaying a temperature substantially indicative of a temperature of said desired area of tissue based on said IR temperature signal and said portion of said tympanic membrane in a field of view of said IR temperature sensor.

* * * * *